United States Patent [19]

Bhattacharya

[11] Patent Number: 5,001,252

[45] Date of Patent: Mar. 19, 1991

[54] UREA COSOLVENTS FOR ORGANIC CARBONATE PROCESS

[75] Inventor: Ajit K. Bhattacharya, Hopewell Junction, N.Y.

[73] Assignee: Texaco Inc., White Plains, N.Y.

[21] Appl. No.: 132,229

[22] Filed: Dec. 11, 1987

[51] Int. Cl.$^5$ .................... C07C 68/00; C07C 69/96
[52] U.S. Cl. ................... 558/277; 558/260; 558/274; 558/275; 558/276
[58] Field of Search ............... 558/274, 275, 277, 260, 558/276

[56] References Cited

U.S. PATENT DOCUMENTS

| | | | |
|---|---|---|---|
| 3,846,468 | 11/1974 | Perrotti et al. | 558/277 |
| 3,980,690 | 9/1976 | Cipriani et al. | 558/277 |
| 4,625,044 | 11/1986 | Curnutt | 558/277 |

*Primary Examiner*—Vivian Garner
*Attorney, Agent, or Firm*—Robert A. Kulason; James J. O'Loughlin; Vincent A. Mallare

[57] ABSTRACT

An organic carbonate such as dimethyl carbonate is prepared by reacting an alcohol such as methanol with carbon monoxide and oxygen in the presence of a catalyst system containing Cu(OMe)Cl as catalyst and a urea or a mixture of ureas as a cosolvent for the catalyst system.

17 Claims, No Drawings

UREA COSOLVENTS FOR ORGANIC CARBONATE PROCESS

BACKGROUND OF THE INVENTION

1. Field Of The Invention

This invention relates to the preparation of organic carbonates. More particularly it relates to urea cosolvents for the preparation of dimethyl carbonate (DMC). DMC may be used as a gasoline extender and octane enhancer, as an organic solvent or as a reactant in place of phosgene in the preparation of isocyanates, polycarbonates, and various agricultural and pharmaceutical intermediates.

Dimethyl carbonate (DMC) may be prepared by the reaction of methanol with carbon monoxide and oxygen in the presence of a catalyst system. Those skilled in the art, constantly seek new or improved catalysts or additives for such catalysts to lower costs, to improve reaction conditions, the yield and rate of production, and to facilitate separation of reactants, products, and catalysts.

Thus, it is an object of this invention to provide an improved method of preparing dimethyl carbonate, lower the cost of the process, substantially increase the yield and rate of production of dimethyl carbonate, and ease the separation of DMC and water from the catalyst system.

2. Disclosure Statement

U.S. Pat. No. 3,114,762 discloses as catalysts, metal salts including chlorides and bromides of platinum and palladium plus an oxidizing agent such as iron or copper salts having the same anion.

U.S. Pat. No. 4,638,076 discloses use of phosphoramide additives for the preparation of organic carbonates.

U.S. Pat. No. 4,636,576 discloses use of cyclic amide additives for the preparation of organic carbonates.

U.S. Pat. No. 3,227,740 discloses as a catalyst, a mercuric halide or a carboxylate.

Saegusa, et.al., J. Org. Chem., 35, 2976–2978 (1970) discloses the reaction of CO with copper alkoxides including the dimethoxide, the diallyloxide, the chloride methoxide and the acetylacetonate methoxide.

Romano, et.al., IEC Prod. Res. Deve. 19, 396–403 (1980) discloses as a catalyst, cuprous chloride/cupric chloride methoxide.

U.S. Pat. No. 4,218,391 discloses as catalysts, salts of metals of Group IB, IIB and VIII, preferably monovalent copper such as cuprous bromide, chloride or perchlorate.

U.S. Pat. No. 4,318,862 discloses as catalysts, salts of metals of Groups IB, IIB or VIII, typically a copper salt such as CuCl.

U.S. Pat. No. 3,846,468 discloses as catalysts, cuprous chloride complexes with an organic ligand such as pyridine, dipyridyl, imidazole, phenanthroline, alkyl, or aryl phosphines, dimethyl sulfoxide, dimethyl formamide, quinuclidine, acetonitrile, benzonitrile, malonitrile, succinodinitrile, or adiponitrile.

U.S. Pat. No. 3,980,690 discloses as a catalyst, a complex of copper chloride and poly-4-vinylpyridine.

Rivetti et al, J. Organometallic Chem, 174 (1979) 221–226 discloses as catalysts, palladium (II) complexes in the presence of ligandp and added bases. Alkyl phosphines are said to inhibit carbonylation almost completely. The presence of tertiary amines enhances the formation of dimethyl carbonate.

U.S. Pat. No. 4,370,275 discloses catalyst compositions containing copper, chemically bonded oxygen, and halogen and a nitrogen base. A typical catalyst contains CuO or Cu(OCl)$_2$ and n-butylamine inter alia. Preferred combinations include: CuCO$_3$, Cu(OH)$_2$, CuCl$_2$ and pyridine hydrochloride etc.

U.S. Pat. No. 4,131,521 discloses an electrochemical process utilizing a non-fluoride halide-containing electrolyte.

U.S. Pat. No. 4,113,762 discloses as a catalyst, a complex of copper (as CuCl) with VCl$_3$, CrCl$_3$, FeCl$_3$, CoCl$_2$, AlCl$_3$, or SiCl$_4$.

U.S. Pat. No., 4,361,519 discloses as catalyst (i) a Bronsted base such as a quaternary ammonium, phosphonium, or sulfonium compound or an alkoxide or hydroxide of alkali metal or alkaline earth metal or a salt of a strong base and a weak acid or amines etc. plus (ii) a Group VIII B element Ru, Rh, Pd, Os, Ir or Pt plus (iii) oxygen plus (IV) a redox catalyst such as a Mn or Co containing catalyst. A typical system includes (i) a pentamethylpiperidine, (ii) PdBr$_2$ and (iii) pyridine adduct of salicylaldehyde - ethylene diamine Co (II) complex.

European Patent 0,071,286 discloses as a catalyst a copper compound such as a halide (in the presence of an amine) plus a sulphone such as dimethyl sulphone or sulfolane.

SUMMARY OF THE INVENTION

This invention is directed to a method of preparing an organic carbonate R$_2$CO$_3$ wherein R is a hydrocarbon group selected from the group consisting of alkyl, alkaryl, aralkyl, cycloalkyl, and aryl hydrocarbon groups. The method comprises:

(a) reacting an alcohol (ROH) with carbon monoxide (CO) and oxygen (O$_2$) in the presence of a catalyst system containing (i) as a catalyst, a copper-nitrogenous ligand complex represented by the formula $L_m Cu(OR)X_{1/n}$ wherein L is a nitrogenous ligand molecule, X is a halide or non-halide anion, m is a number of about 0 to about 4, n is equal to 1, 2 or 3 and R is a hydrocarbon group selected from the group consisting of alkyl, alkaryl, aralkyl, cycloalkyl and aryl; and (ii) as a cosolvent, as well as a heat transfer fluid and a catalyst carrier, a thermally and chemically stable urea cosolvent having a boiling point higher than that of the organic carbonate formed; and (b) recovering the organic carbonate product.

Or, more specifically, the method may comprise:

(a) reacting an alcohol (ROH) with carbon monoxide and oxygen in the presence of a catalyst system containing:

(i) as a catalyst, a copper hydrocarbonoxy salt Cu(OR')X wherein R' is a hydrocarbon group selected from the group consisting of alkyl, alkaryl, aralkyl, cycloalkyl, and aryl and X is an anion such as chloride, alkoxide or sulfate; and (ii) as a cosolvent, as well as a heat transfer fluid and a catalyst carrier, a thermally and chemically stable urea cosolvent having a boiling point higher than that of the organic carbonate formed; and (b) recovering the organic carbonate product.

DESCRIPTION OF THE INVENTION

In preparing organic carbonates according to the present invention, a urea cosolvent for the catalyst is used which substantially increases the yield and rate of the organic carbonate. The organic carbonate, e.g., dimethyl carbonate, is prepared by:

(a) reacting an alcohol with carbon monoxide and oxygen in the presence of a catalyst system containing (i) as a catalyst, a copper-nitrogenous ligand complex represented by the formula
$L_m Cu(OR)X_{1/n}$

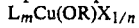

wherein L is a nitrogenous ligand molecule, X is a halide or non-halide anion, m is a number of about 0 to about 4, n is equal to 1, 2 or 3 and R is a hydrocarbon group selected from the group consisting of alkyl, alkaryl, aralkyl, cycloalkyl and aryl; and (ii) as a cosolvent, as well as a heat transfer fluid and a catalyst carrier, a thermally and chemically stable urea cosolvent having a boiling point higher than that of the organic carbonate formed; and (b) recovering the organic carbonate product.

Or, more specifically, the method may comprise:

(a) reacting an alcohol (ROH) with carbon monoxide and oxygen in the presence of a catalyst system containing (i) as a catalyst, a copper hydrocarbonoxy salt Cu(OR')X wherein R' is a hydrocarbon group selected from the group consisting of alkyl, alkaryl, aralkyl, cycloalkyl, and aryl and X is an anion such as a chloride, alkoxide or sulfate; and (ii) as a cosolvent, as well as a heat transfer fluid and a catalyst carrier, a thermally and chemically stable urea cosolvent having a boiling point higher than that of the organic carbonate formed; and (b) recovering the organic carbonate product.

The halide anions may be any of the halide ions including F, Cl, Br and I and the non-halide anions may be selected from the group of non-halide anions consisting of $NO_2$, $NO_3$, $OCH_3$, $Ch_3COO$, OH, O, $CO_3$, $SO_4$, $HSO_4$, $PO_4$, $H_2PO_4$ and $HPO_4$.

The cosolvent for the catalyst may be a urea of the formula $$R^1 \diagdown \quad \underset{\|}{O} \quad \diagup R^3$$
$$\quad N - C - N$$
$$R^2 \diagup \qquad \diagdown R^4$$

(I)

where $R^1$, $R^2$, $R^3$ and $R^4$ are each H, a ($C_1-C_8$) alkyl group or a ($C_1-C_8$) alkylene group.

The charge alcohol which may be employed in practice, of the method of this invention may include those characterized by the formula ROH.

In the above compound, R may be a hydrocarbon group selected from the group consisting of alkyl, aralkyl, cycloalkyl, aryl, and alkaryl, including such radicals when inertly substituted. When R is alkyl, it may typically be methyl, ethyl, n-propyl, iso-propyl, n-butyl, i-butyl, sec-butyl, amyl, octyl, decyl, octadecyl, etc.

When R is aralkyl, it may typically be benzyl, beta-phenylethyl, etc. When R is cycloalkyl, it may typically be cyclohexyl, cycloheptyl, cyclooctyl, 2-methylcycloheptyl, 3-butylcyclohexyl, 3-methylcyclohexyl, etc. When R is aryl, it may typically be phenyl, naphthyl, etc. When R is alkaryl, it may typically be tolyl, xylyl, etc. R may be inertly substituted i.e. it may bear a non-reactive substituent such as alkyl, aryl, cycloalkyl, ether, etc. Typically inertly substituted R groups may include 2-ethoxyethyl, carboethoxymethyl, 4-methyl cyclohexyl, etc. The preferred R groups may be lower alkyl, i.e. $C_1-C_{10}$ alkyl, groups including methyl, ethyl, n-propyl, i-propyl, butyls, amyls, hexyls, octyls, decyls, etc. R may preferably be methyl.

The charge alcohol may be a phenol, i.e., when R is aryl. The notation ROH is intended to include polyols such as ethylene glycol, glycerine, sorbitol, poly (oxyalkylene) polyols, etc; in these latter compounds, the formula may more typically be represented as $R(OH)_n$ wherein R is derived from an alkyl group and n is an integer, typically 2–10.

The charge alcohols which may be employed include those listed below in Table I.

TABLE I methanol
ethanol
n-propanol
i-propanol
benzyl alcohol
phenol
ethylene glycol
glycerine
sorbitol
poly(oxyethylene-10) glycol The preferred alcohols are the lower ($C_1-C_4$) alkanols; and the most preferred is methanol.

The carbon monoxide charge which may be employed may be a pure gas. More commonly it may be a synthesis gas of high purity from which most of the hydrogen and carbon dioxide have been removed.

The catalyst, i.e., copper hydrocarbonoxy salt Cu-(OR')X may be one wherein X is a fluoride, chloride, bromide, sulfate or nitrate. Preferably X is a non-halide anion such as nitrate. R' may be selected from the same group as R; and preferably R' is lower, alkyl i.e. $C_1-C_{10}$ alkyl. Preferably R' is methyl. Typical compounds may include those listed below in Table II.

TABLE II

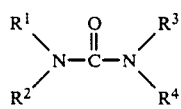

The copper salt catalyst system containing Cu(II)(OMe)Cl/Cu(I)Cl is only sparingly soluble in methanol and the rate of DMC formation is undesirably low. This invention relates to the large increase in the yield and rate of organic carbonate formation in the presence of a urea cosolvent. Thus, the rate of DMC production is significantly augmented in the presence of a urea such as 1,3-dimethylpropyleneurea (DMPU), as a cosolvent for the catalyst concerned. According to the present invention, it has been found that the rate of DMC formation in DMPU is about 2 to about 4 times higher than that under similar conditions in methanol or tetraethylsulfamide respectively. An additional advantage of DMPU (or similar urea cosolvents) over various lower boiling point solvents (such as lower hydrocarbons, ethers, and acetonitrile) is that DMPU (bp 146° C./44 mm) is less volatile and remains with the catalyst during any subsequent separation of the reaction mixture by a flash or distilation method.

The cosolvent for the catalyst may be a urea of formula (I)

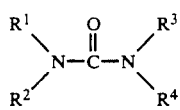

where $R^1$, $R^2$, $R^3$ and $R^4$ are each H, a ($C_1$–$C_8$) alkyl group or a ($C_1$–$C_8$) alkylene group.

The urea compound, according to the present invention may be tetramethylurea, tetraethylurea, 1,3-dimethyl-2-imidazolidinone (DMI) or 1,3-dimethylpropyleneurea (DMPU) or a mixture thereof.

And, according to formula (I) above, the ureas may be represented as follows:

Tetramethylurea (where $R^1$, $R^2$, $R^3$ and $R^4$ are each $CH_3$)

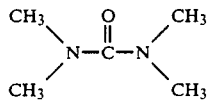

Tetraethylurea (where $R^1$, $R^2$, $R^3$ and $R^4$ are each $c_2Hhd 5$)

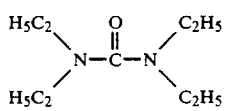

1,3-dimethylpropyleneurea (where $R^1$ and $R^3$ are each $CH_3$ and $R^2$ and $R^4$ combined are trimethylene)

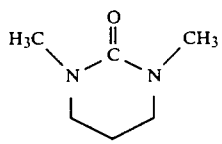

1,3-dimethyl-2-imidazolidinone (where $R^1$ and $R^3$ are each $CH_3$, and $R^2$ and $R^4$ combined are ethylene)

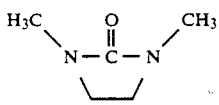

1,3-dimethylurea (where $R^1$ and $R^3$ are each H, and $R^2$ and $R^4$ are each $CH_3$).

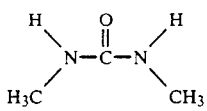

1,3-diethylurea (where $R^1$ and $R^3$ are each H, and $R^2$ and $R^4$ are each $C_2H_5$)

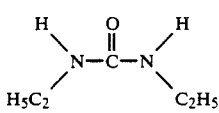

The catalyst system may be present in the reaction mixture in an amount of about 0.1 to about 50 parts, preferably about 0.1 to about 20 parts, and more preferably about 10 parts per 100 parts of charge methanol.

The practice of the method of this invention may be carried out by adding 100 parts of an optimum mixture of the alcohol ROH, such as methanol and a urea cosolvent to the reaction mixture. The preferred cosolvents may be 1,3-dimethylpropyleneurea (DMPU), 1,3-dimethyl-2-imidazolidinone (DMI), tetramethylurea, 1,3-dimethylurea, 1,3-diethylurea or a mixture thereof. The weight percent (wt.%) of cosolvent in methanol may vary from about 1.0 to about 95 percent, preferably about 50 percent, and more preferably about 75 percent. The catalyst system may then be added. The system may then optionally be subjected to an inert gas typically nitrogen at a partial pressure of 5–1000 psi, preferably 100–300 psi, e.g., about 25 psi and heated to 20° C.–170° C., preferably 80–120° C., e.g., about 100° C. at a total pressure of 10–2000 psi, preferably 150–600 psi, e.g., about 50 psi over 0.25–2 hours, e.g., about 0.5 hour.

Carbon monoxide-containing gas may then be admitted to a carbon monoxide partial pressure of 5–3000 psi, preferably 100–900 psi, e.g., 350 psi over 0.25–10 hours, e.g., 1 hour.

During this period, the following reaction occurs in the preferred embodiment:

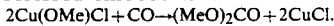

At the end of this time, the reaction mixture may be rapidly cooled to 20° C.–b 90° C., e.g., 25° C. at a total pressure of 15–3000 psi, e.g., 300 psi.

The reaction mixture may be flashed under reduced pressure to remove gases, methanol, DMC and water or depressured and then distilled to azeotropically distill off various fractions containing methanol, dimethyl carbonate and water. The product may be further treated to effect greater purification of the impure dimethyl carbonate.

The residual catalyst system (0.1–50 parts, e.g., 10 parts) may be regenerated as by bubbling oxygen-containing gas, typically air at 20° C.–65° C., e.g., 45° C. for 1–20 hours, e.g., 6 hours in the presence of an alcohol-cosolvent combination typically methanol-1,3-dimethylpropyleneurea (3 to 1) in an amount of 100 parts.

During this regeneration step, the following reaction occurs in the preferred embodiment:

At the end of the regeneration period, the catalyst in methanol may be recycled if the water content is less than about 1.0 wt.%. If more water than this is present, the catalyst and the cosolvent may be dried by depressurizing and flashing all volatiles including DMC and water and the anhydrous catalyst system may be recycled using anhydrous methanol.

Practice of the method of this invention will be apparent to those skilled in the art from the following examples, wherein as elsewhere in this specification, all parts are parts by weight unless otherwise noted.

EXAMPLES I–III

In these examples there was added to the reaction vessel 135 ml of anhydrous methanol, 14.0g (0.1077 mol) of anhydrous Cu(OMe)Cl and 45 ml of cosolvent (i.e., tetraethylsulfamide, tetramethylurea, or 1,3-dimethylpropyleneurea). In Example R, 180 ml of methanol was used and in Examples I–III, the methanol and cosolvent were added in a methanol to cosolvent ratio of about 3:1.

In each of the Examples, the procedure and conditions were the same except that the cosolvent was different.

The reaction mixture was pressurized to 25 psig with nitrogen, heated to 100° C. and maintained at 100° C. for 0.5 hour. The pressure was increased to 400 psig with carbon monoxide and stirring was continued for 0.25 hour. The reaction mixture was then cooled to room temperature, and depressurized. The reaction mixture was distilled with added methanol (200 ml) to recover azeotrope containing methanol and dimethyl carbonate. Analysis by gas chromatography for each run indicated the yields (based on copper) shown below in Table III.

TABLE III

EVALUATION OF HIGH BOILING COSOLVENTS FOR DMC PRODUCTION

| Example | Solvent (vol:vol) | B.P.(° C.) of Cosolvent | % Yield of DMC[1,2] |
|---|---|---|---|
| R[3] | Methanol (neat) | 63° | 45.5 |
| I | MeOH-Tetraethylsulfamide (3:1) | 250° | 25.0 |
| II | MeOH-Tetramethylurea (3:1) | 177° | 65.5 |
| III | MeOH-1,3-Dimethylpropyleneurea (3:1) | 146°/44 mm | 96.0 |

[1] Reaction conditions: Cu(II)(OMe)Cl(14.0 g)/180 ml solvent/100° C./400 psig N$_2$: CO(1:7)/0.25 hour
[2] Gas chromatographic analysis has been employed to determine the yield based on copper and 100% DMC selectivity.
[3] Reference solvent which was compared with present cosolvents.

As shown in Table III above, the addition of a urea cosolvent of the present invention greatly increased the yield of dimethyl carbonate (DMC). In fact, the yield was more than doubled in the presence of DMPU cosolvent when compared with methanol as a solvent. A rate-retarding effect is exhibited with a sulfamide cosolvent. It is apparent that the process of this invention makes it possible to obtain higher yields of DMC in shorter times, i.e., to increase the rate of formation of desired DMC.

Although this invention has been illustrated by reference to specific embodiments, it will be apparent to those skilled in the art that various changes and modifications may be made which already fall within the scope of this invention.

We claim:

1. A method of preparing an organic carbonate, R$_2$CO$_3$ which comprises:
   (a) reacting an alcohol, ROH, with carbon monoxide and oxygen in the presence of a catalyst system containing
   (i) as a catalyst a copper-nitrogenous ligand complex represented by the formula

wherein L is a nitrogenous ligand molecule, X is a halide or non-halide anion, m is a number of about 0 to about 4, n is equal to 1, 2 or 3 and R and R' are each a hydrocarbon group selected from the group consisting of alkyl, alkaryl, aralkyl, cycloalkyl and aryl; and
   (ii) as a cosolvent, as well as a heat transfer fluid and a catalyst carrier, a thermally and chemically stable urea cosolvent having the formula

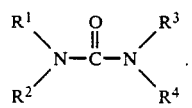

wherein R$^1$, R$^2$, R$^3$ and R$^4$ are each H, a (C$_1$–C$_8$) alkyl group and when combined R$^1$ and R$^3$ or R$^2$ and R$^4$ are a (C$_1$–C$_8$) alkylene group, and a boiling point higher than that of the organic carbonate formed; and
   (b) recovering the organic carbonate product.

2. The method of claim 1, wherein said non-halide anion X is selected from the group of non-halide anions consisting of NO$_2$, NO$_3$, OCH$_3$, CH$_3$COO, OH, O, CO$_3$, SO$_4$, HSO$_4$, PO$_4$, H$_2$PO$_4$ and HOP$_4$.

3. The method of claim 1, wherein the cosolvent is tetramethylurea

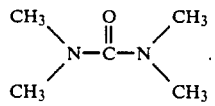

4. The method of claim 1, wherein the cosolvent urea is tetraethylurea

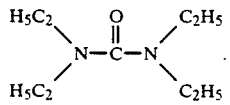

5. The method of claim 1, wherein the cosolvent is 1,3-dimethylpropyleneurea

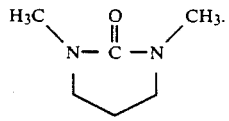

6. The method of claim 1, wherein the cosolvent is 1,3-dimethyethyleneurea

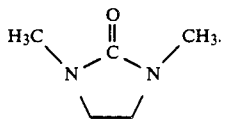

7. The method of claim 1, wherein the cosolvent is 1,3-dimethylurea

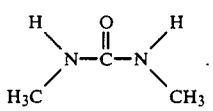

8. The method of claim 1, wherein the cosolvent is 1,3-diethylurea

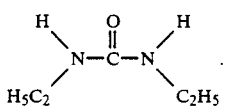

9. The method of claim 1, wherein the cosolvent is a mixture of 1,3-dimethylurea and 1,3-diethylurea.

10. The method of claim 1, wherein the method is carried out at a temperature of 20° C. to 170° C., and a pressure of 10 to 2000 psi for a period of 0.25 to 2.0 hours.

11. The method of claim 1, wherein said alcohol is methanol nd the corresponding organic carbonate is dimethyl carbonate.

12. The method of claim 11, wherein between about 0.1 and about 50 parts of said catalyst system per 100 parts of methanol are present.

13. The method of claim 12, wherein the method is carried out at a temperature of 80° C. to 120° C. and a pressure of 150 to 600 psi for a period of about 0.5 hour.

14. The method of claim 12, wherein the method is carried out at a temperature of about 90° C. and a pressure of about 150 psi for a period of about 0.5 hour.

15. The method of claim 11, wherein the weight percent of cosolvent in said methanol ranges from about 1.0 to about 95 wt.%.

16. The method of claim 15, wherein the weight percent of cosolvent in said methanol is about 50 wt.%.

17. The method of claim 15, wherein weight of cosolvent in said methanol is about 75 wt.%.

* * * * *